(12) United States Patent
Landa

(10) Patent No.: US 7,306,612 B1
(45) Date of Patent: Dec. 11, 2007

(54) CRANIAL SPINAL COLUMN SUPPORT ASSEMBLY

(76) Inventor: Jose S. Landa, 735 Delorean Dr., North Las Vegas, NV (US) 89031

( * ) Notice: Subject to any disclaimer, the term of this patent is extended or adjusted under 35 U.S.C. 154(b) by 776 days.

(21) Appl. No.: 10/683,638

(22) Filed: Oct. 9, 2003

(51) Int. Cl.
*A61B 19/00* (2006.01)

(52) U.S. Cl. .......................................... 606/130; 5/622

(58) Field of Classification Search ............... 606/130; 5/622
See application file for complete search history.

(56) References Cited

U.S. PATENT DOCUMENTS

| | | | |
|---|---|---|---|
| 1,171,713 A * | 2/1916 | Gilderson | .................. 606/245 |
| 2,398,940 A | 4/1946 | Jones | |
| 3,608,103 A * | 9/1971 | Seid | ............................. 5/661 |
| 4,064,401 A | 12/1977 | Marden | |
| 5,214,815 A | 6/1993 | Agbodoe et al. | |
| 5,947,981 A | 9/1999 | Cosman | |
| 6,143,003 A * | 11/2000 | Cosman | ...................... 606/130 |
| 6,355,049 B1 | 3/2002 | Gill | |
| 6,460,207 B1 | 10/2002 | Papay et al. | |
| 6,565,577 B2 * | 5/2003 | Cosman | ...................... 606/130 |

* cited by examiner

*Primary Examiner*—Michael J. Hayes
*Assistant Examiner*—Michael Mendoza

(57) ABSTRACT

A cranial spinal column support assembly includes a base having a first end, a second end, an upper surface and a lower surface. A support frame is attached to and extends upwardly from the upper surface. The support frame is positioned generally adjacent to the first end of the base. A mounting is positioned on the support frame and is selectively positioned between an upper portion of the support frame and a lower portion of the support frame. A securing member is adapted for releasably securing the mounting to the frame in a fixed position. A head support is mounted to and extends outwardly away from the mounting. The head support includes a face receiving member for receiving a head in a downward facing position.

15 Claims, 7 Drawing Sheets

CRANIAL SPINAL COLUMN SUPPORT ASSEMBLY

BACKGROUND OF THE INVENTION

1. Field of the Invention

The present invention relates to head support devices and more particularly pertains to a new head support device for supporting a head to stabilize the cranial spinal column while a patient requiring such support is in a prone position.

2. Description of the Prior Art

The use of head support devices is known in the prior art. U.S. Pat. No. 2,398,940 a padded head support for supporting a head while a patient receives treatment. Another type of head support device is U.S. Pat. No. 6,460,207 which has a structure for preventing sudden infant death syndrome. U.S. Pat. No. 6,355,049 includes a structured for supporting a head in a fixed position for stereotatic diagnosis and treatment. Yet another example is U.S. Pat. No. 5,947,981 for supporting the head and neck of a patient in a prone position.

While these devices fulfill their respective, particular objectives and requirements, the need remains for a device that allows a patient to receive radiation treatments to their cranial spinal column. The device should allow the patient to be in a prone position and will support the patient's head in a natural position that is stabilized.

SUMMARY OF THE INVENTION

The present invention meets the needs presented above by providing a head support attached to base that allows a patient to lie in a prone position on the device so that their head is comfortably positioned in head support a stable manner.

Another object of the present invention is to provide a new head support device wherein the head support is adjustable such that a proper alignment of the cranial spinal column is attained.

Still another object of the present invention is to provide a new head support device that also includes a space for receiving an x-ray slide such that an x-ray image may be taken while the head is in a stabilized condition.

To this end, the present invention generally comprises a base having a first end, a second end, an upper surface and a lower surface. A support frame is attached to and extends upwardly from the upper surface. The support frame is positioned generally adjacent to the first end of the base. A mounting is positioned on the support frame and is selectively positioned between an upper portion of the support frame and a lower portion of the support frame. A securing member is adapted for releasably securing the mounting to the frame in a fixed position. A head support is mounted to and extends outwardly away from the mounting. The head support includes a face receiving member for receiving a head in a downward facing position.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
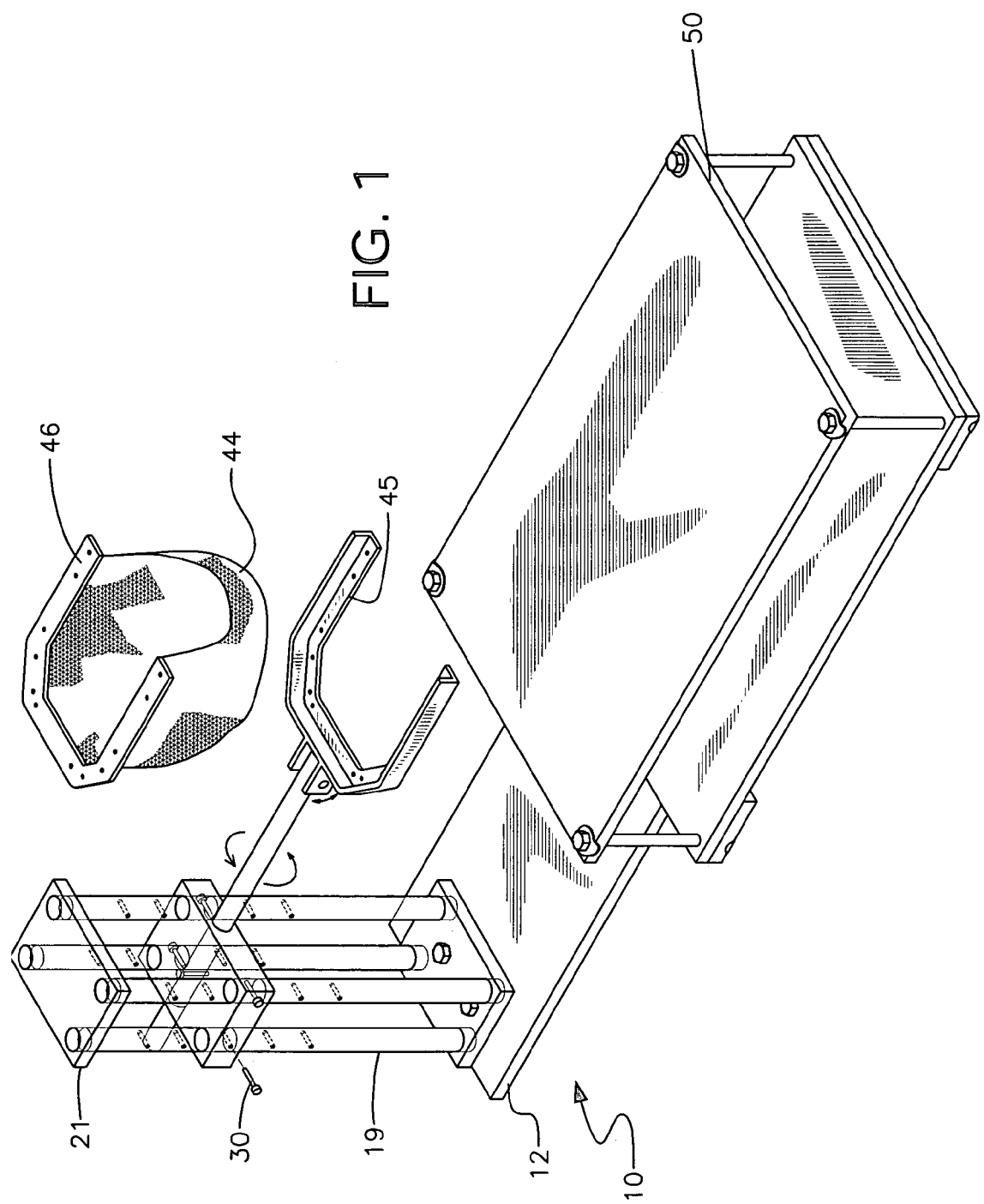
FIG. 1 is a schematic perspective view of a cranial spinal column support assembly according to the present invention.
Figure 2:
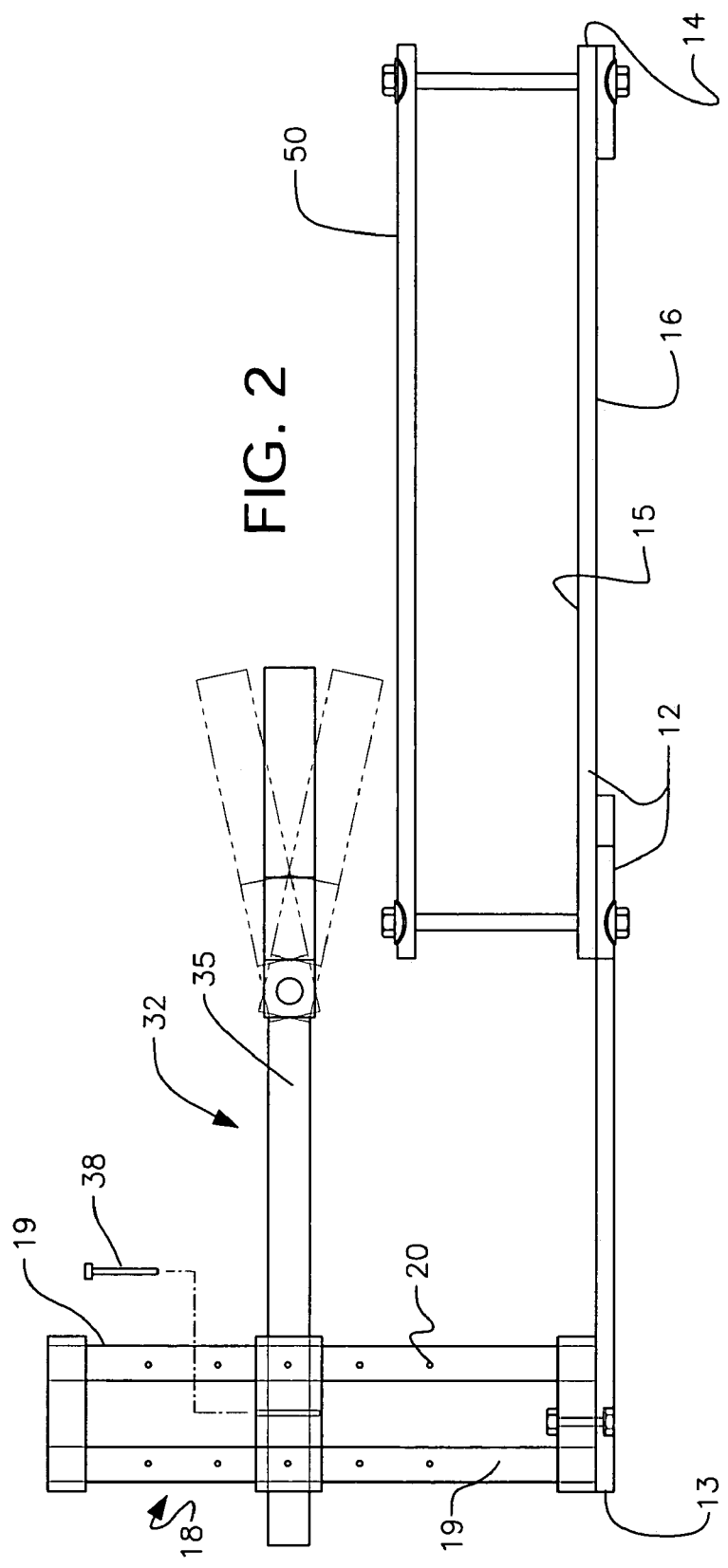
FIG. 2 is a schematic side view of the present invention.
Figure 3:
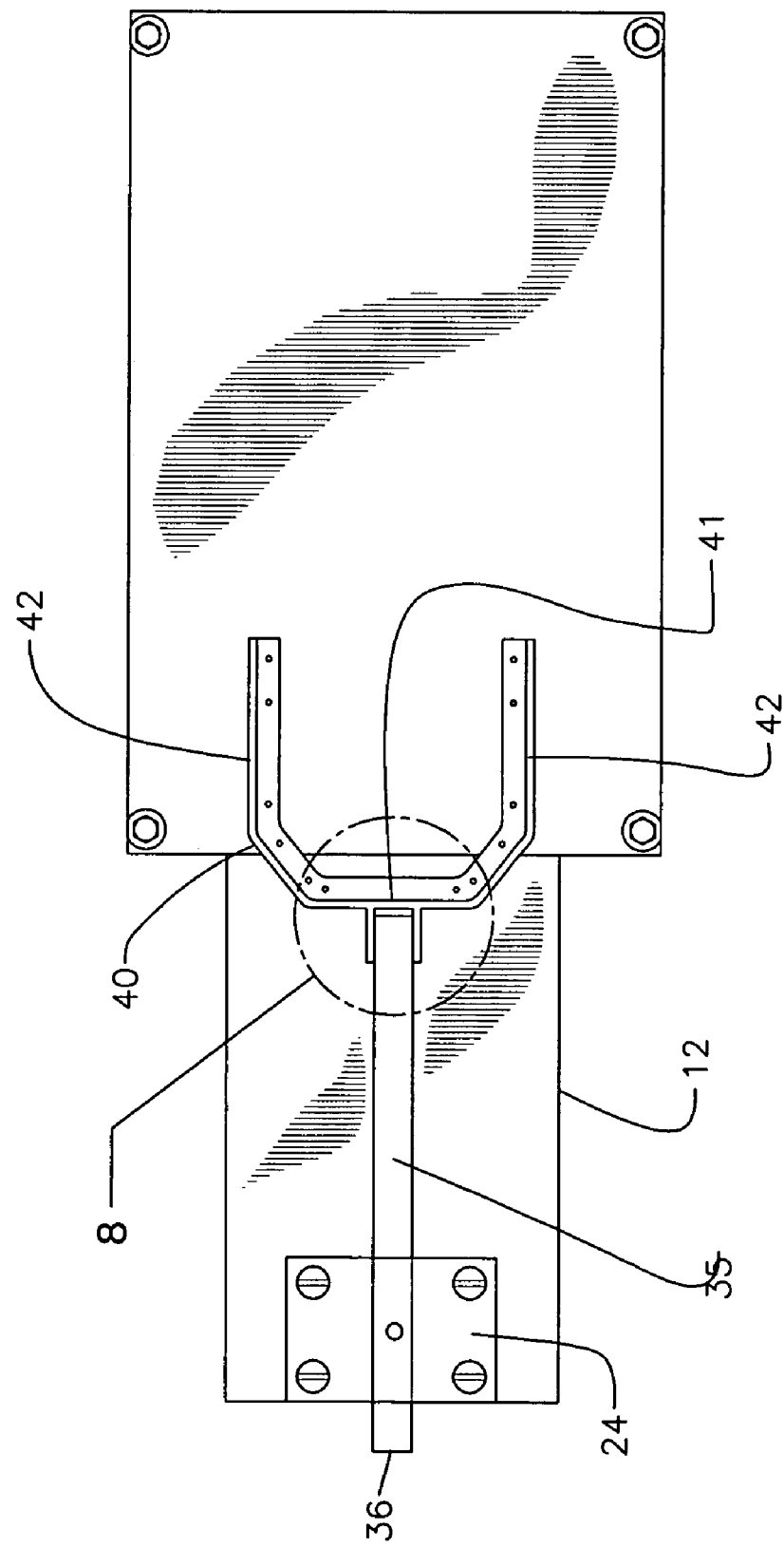
FIG. 3 is a schematic top view of the present invention.
Figure 4:
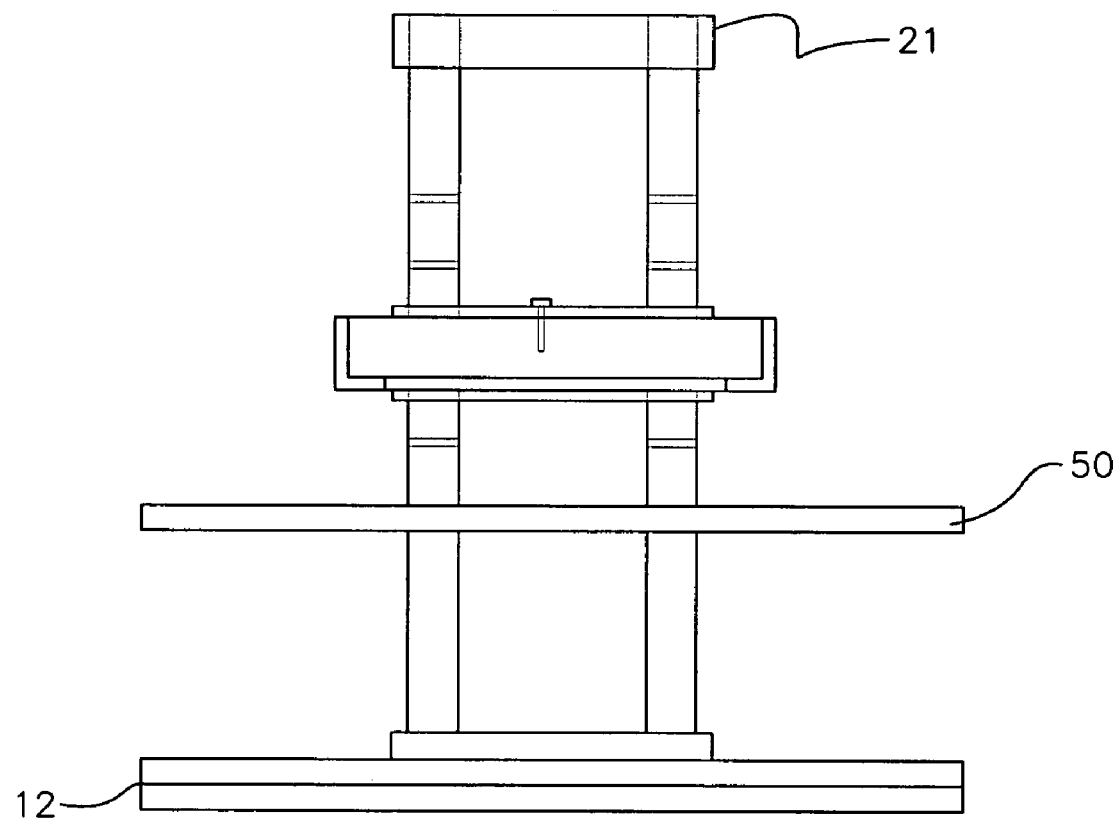
FIG. 4 is a schematic right side view of the present invention.
Figure 5:
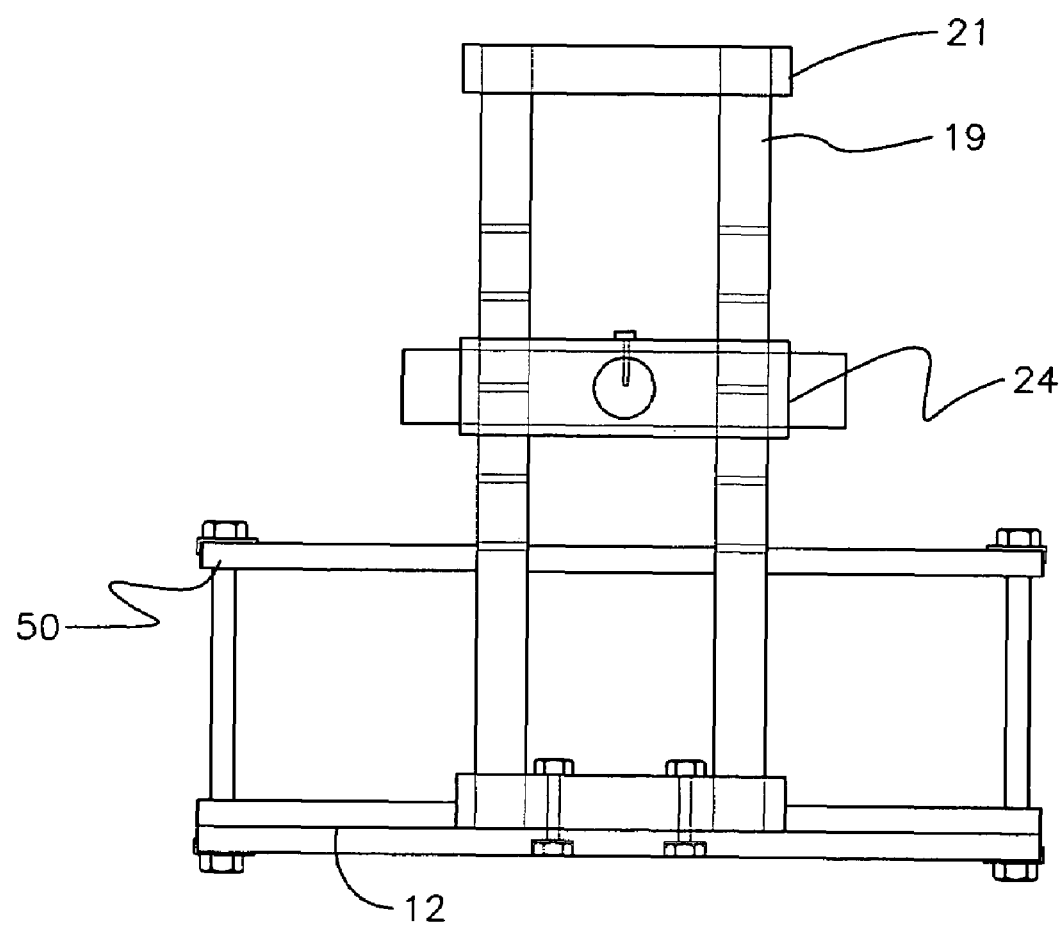
FIG. 5 is a schematic left view of the present invention.
Figure 6:
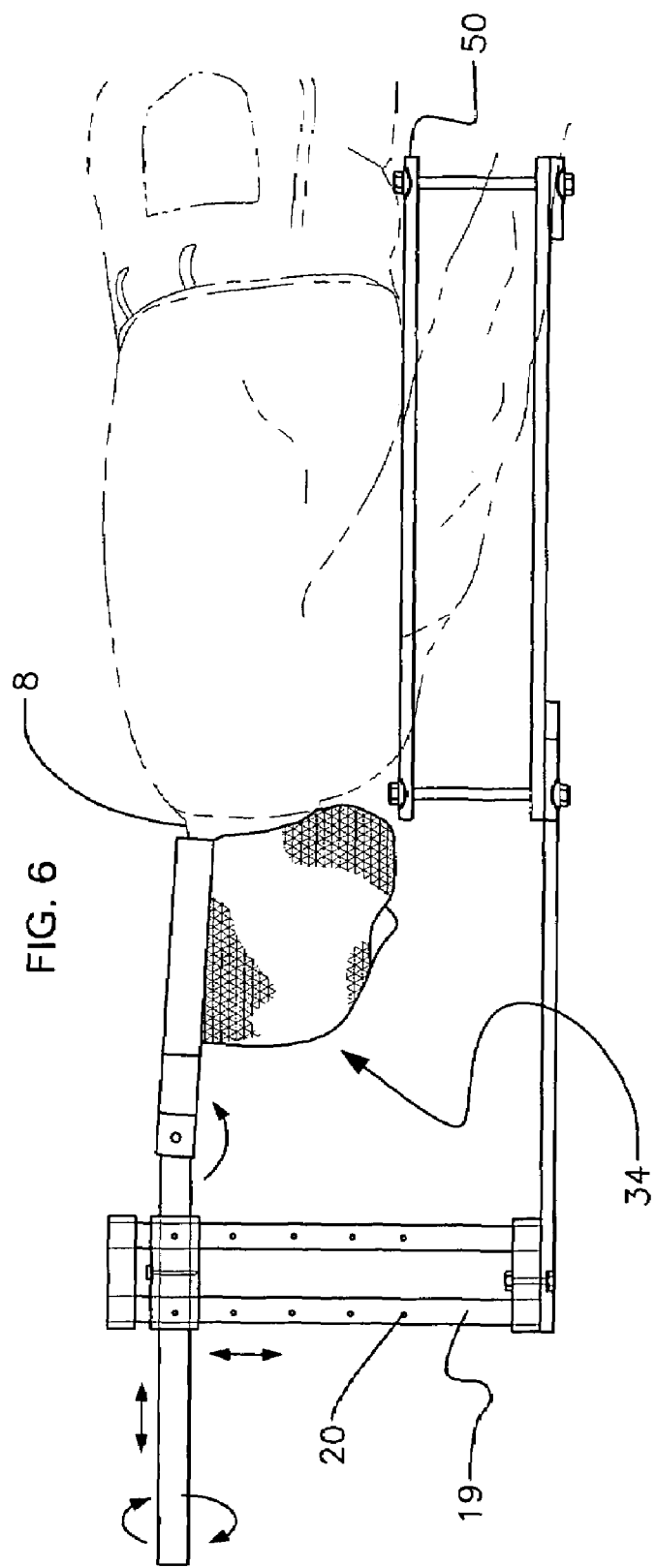
FIG. 6 is a schematic side view of the present invention.
Figure 7:
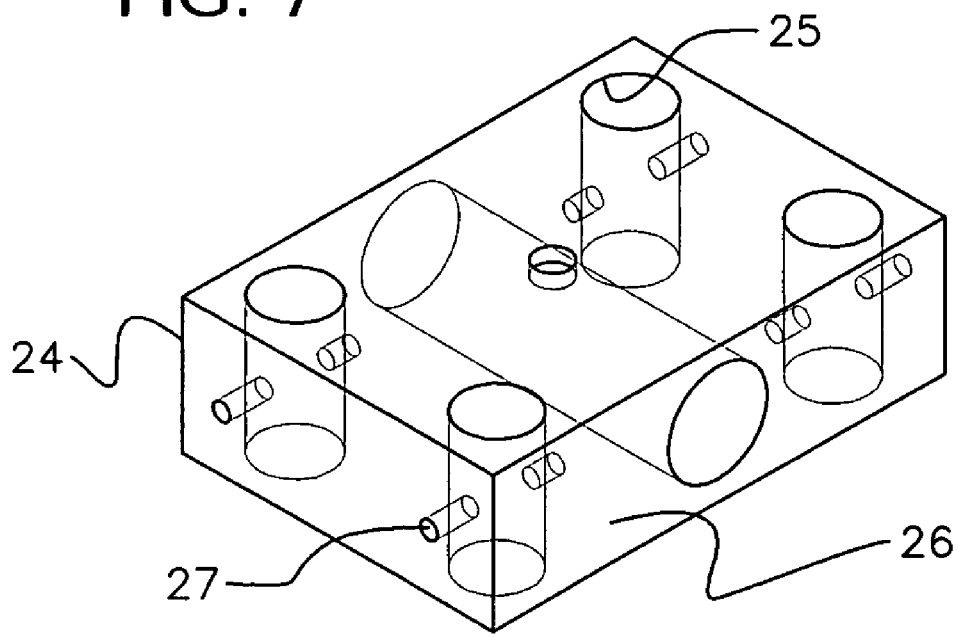
FIG. 7 is a schematic perspective view of the plate of the present invention.
Figure 8:
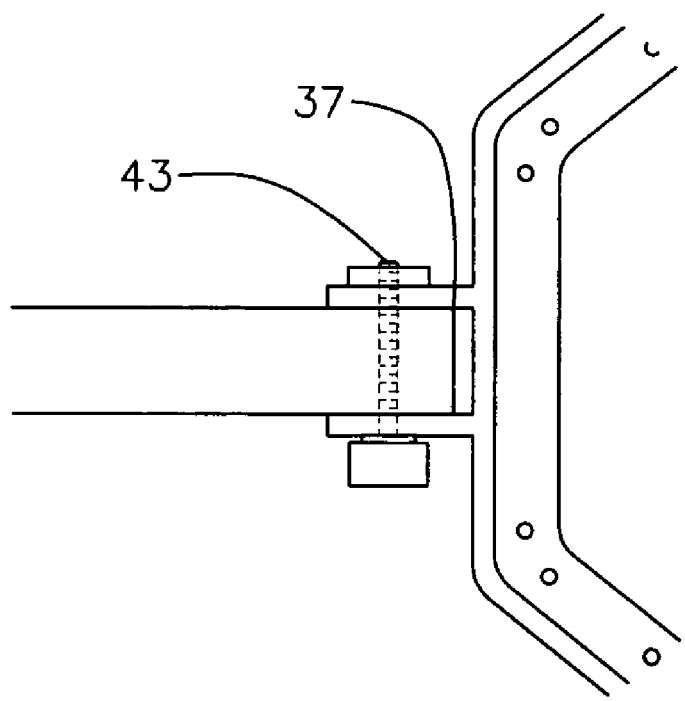
FIG. 8 is a schematic top enlarged view of the rod and U-shaped member of the present invention.

With reference now to the drawings, and in particular to FIGS. 1 through 8 thereof, a new head support device embodying the principles and concepts of the present invention and generally designated by the reference numeral 10 will be described.

As best illustrated in FIGS. 1 through 8, the cranial spinal column support assembly 10 generally includes a base 12 having a first end 13, a second end 14, an upper surface 15 and a lower surface 16. A support frame 18 is attached to and extends upwardly from the upper surface 15. The support frame 18 is positioned generally adjacent to the first end 13 of the base 12. The support frame 18 includes a plurality of vertically orientated columns 19. Each of the columns 19 has a plurality of apertures 20 extending therethrough. The apertures 20 are each horizontally aligned with one of the apertures 20 in each of the columns 19 and it is preferred that each of the columns 19 has at least three apertures 20 extending therethrough. The plurality of columns 19 includes four columns 19 positioned in a generally rectangular configuration. A panel 21 is attached to an upper end of each of columns 19. The columns 19 each preferably have a height between 6 inches and 18 inches.

A mounting 24 is positioned on the support frame 18 and is selectively positioned between an upper portion of the support frame 18 and a lower portion of the support frame 18. The mounting 24 comprises a plate having a plurality of openings 25 extending therethrough. Each of the columns 19 extends through one of the openings 25 in the plate, or mounting 24, such that the plate 24 is moveably mounted on the columns 19 in a substantially horizontal orientation. The plate 24 has a peripheral edge 26. Each of plurality of bores 27 extends into the peripheral edge 26 and into one of the openings 25, wherein each of the bores 27 may be selectively aligned with one of the apertures 20.

A securing member 30 is adapted for releasably securing the mounting 24 to the frame 18 in a fixed position. The securing member 30 includes a plurality of pins. Each of the pins, or securing member(s) 30, is removably extendable into one of the bores 27 and a correspondingly aligned one of the apertures 20.

A head support 32 is mounted to and extends outwardly away from the mounting 24. The head support 32 includes a face receiving member 34 for receiving a face in a downward facing position. The head support 32 includes an elongated rod 35 having a first end 36 and a second end 37. The first end 36 is extended into and rotatably coupled to the plate 24 such that the rod 35 extends away from the plate 24 in a substantially horizontal orientation and generally toward the second end 14 of the base 12. A pin 38 may be extended through the plate 24 and into the rod 35 for preventing rotation of the rod 35. A face holding assembly 40 is pivotally coupled to and extends away from the second end 37 of the rod 35.

The face holding assembly 34 includes a U-shaped member 40 having a central portion 41 and a pair of arms 42 that are attached to and extend away from the central portion 41. The arms 42 each have a length generally between 6 inches and 12 inches and the central portion 41 has a length generally between 4 inches and 8 inches. The central portion 41 is attached to the rod 35 and is horizontally orientated. The central portion 41 is attached to the U-shaped member by a pivot member 43. Ideally, the pivot member 43 may be selectively tightened to lock the U-shaped member 40 in a fixed position with respect to the rod 35. A flexible material 44 is removably coupled to and extends along a length of the U-shaped member 40. Ideally, the U-shaped member 40 has an inner flange 45 extending along a length of the U-shaped member 40. The flexible material 44 is attached to a guide 46 having the same shape as the flange 45 and the guide 46 may be attached to the flange 45 with conventional mechanical fasteners such as screws or hook and loop securing members. The flexible material 44 is ideally an air-permeable mesh material that may or may not include padding. The flexible material 44 hangs downward from the U-shaped member to cradle the face in a comfortable manner. To support a head, the face may be positioned between the arms 42 on the flexible material 44.

The materials used of the current assembly 10 may be any conventional material, though a rigid plastic is a preferred material for the support frame, head support and mounting.

Preferably, a platform 50 is attached to the upper surface 15 of the base such that the platform 50 is spaced from the upper surface 15. The platform 50 extends from the second end 14 of the base 12 and toward, but spaced from, the support frame 18. The platform 50 is substantially horizontally orientated. The space between the base 12 and the platform 50 is preferably between 2 inches and 6 inches.

In use, a patient who is going to have radiation treatments to their cranial spinal column 8 lies on assembly in a prone position and places their face on the flexible material 44. The mounting 24 may be adjusted on the support frame 18 so that the spinal column 8 is positioned as needed for the treatment. The rod 35 may be freely extended completely through the plate 24 as needed to move the head support 34 nearer, or further away from the platform. The rod 32 may also be rotated as needed in order to rotate the spinal column 8. The assembly 10 holds the patient in a natural and steady position so that the treatment may be performed accurately and quickly. The space between the platform 50 and the base 12 may be used for the positioning of x-ray slides if such are needed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A head and neck immobilization device for preventing the movement of a cranial spinal column during radiation applications to the cranial spinal column, said device comprising:

a base having a first end, a second end, an upper surface and a lower surface;

a support frame being attached to and extending upwardly from said upper surface, said support frame being positioned generally adjacent to said first end of said base, said support frame including a plurality of vertically orientated columns, each of said columns having a plurality of apertures extending therethrough, each of said apertures being horizontally aligned with one of said apertures in each of said columns, each of said columns having at least three apertures extending therethrough;

a mounting being positioned on said support frame and being selectively positioned between an upper portion of said support frame and a lower portion of said support frame, said mounting comprising a plate having a plurality openings extending therethrough, each of said columns extending through one of said openings in said plate such that said plate is moveably mounted on said columns in a substantially horizontal orientation, said plate having a peripheral edge, each of a plurality of bores extending into said peripheral edge and into one of said openings, wherein each of said bores may be selectively aligned with one of said apertures;

a securing member being adapted for releasably securing said mounting to said frame in a fixed position, said securing member including a plurality of pins, each of said pins being removably extendable into one of said bores and a correspondingly aligned one of said apertures; and a head support being mounted to and extending outwardly away from said mounting, said head support including a face receiving member for receiving a head in a downward facing position.

2. The device of claim 1, wherein said plurality of columns includes four columns positioned in a generally rectangular configuration, a panel being attached to an upper end of each of columns.

3. The device of claim 1, wherein said head support includes an elongated rod having a first end and a second end, said first end being extended into plate such that said rod extends away from said plate in a substantially horizontal orientation and generally toward said second end of said base, a face holding assembly being pivotally coupled to and extending away from said second end of said rod.

4. The device of claim 3, wherein said face holding assembly includes a U-shaped member having a central portion and a pair of arms being attached to and extending away from said central portion, wherein said central portion is attached to said rod and is horizontally orientated, a flexible material being removably coupled to and extends along a length of said U-shaped member, wherein the head may be positioned between the arms and on said flexible material.

5. The device of claim 1, further including a platform being attached to said upper surface of said base such that said platform is spaced from said upper surface, said platform extending from said second end of said base toward said support frame, said platform being substantially horizontally orientated.

6. The device of claim 3, further including a platform being attached to said upper surface of said base such that said platform is spaced from said upper surface, said platform extending from said second end of said base toward said support frame, said platform being substantially horizontally orientated.

7. A head and neck immobilization device for preventing the movement of a cranial spinal column during radiation applications to the cranial spinal column, said device comprising:

a base having a first end, a second end, an upper surface and a lower surface;

a support frame being attached to and extending upwardly from said upper surface, said support frame being positioned generally adjacent to said first end of said base, said support frame including a plurality of vertically orientated columns, each of said columns having a plurality of apertures extending therethrough, each of said apertures being horizontally aligned with one of said apertures in each of said columns, each of said columns having at least three apertures extending therethrough, said plurality of columns including four columns positioned in a generally rectangular configuration, a panel being attached to an upper end of each of columns;

a mounting being positioned on said support frame and being selectively positioned between an upper portion of said support frame and a lower portion of said support frame, said mounting comprising a plate having a plurality openings extending therethrough, each of said columns extending through one of said openings in said plate such that said plate is moveably mounted on said columns in a substantially horizontal orientation, said plate having a peripheral edge, each of plurality of a bores extending into said peripheral edge and into one of said openings, wherein each of said bores may be selectively aligned with one of said apertures;

a securing member being adapted for releasably securing said mounting to said frame in a fixed position, said securing member including a plurality of pins, each of said pins being removably extendable into one of said bores and a correspondingly aligned one of said apertures;

a head support being mounted to and extending outwardly away from said mounting, said head support including a face receiving member for receiving a head in a downward facing position, said head support including;

an elongated rod having a first end and a second end, said first end being extended into and rotatably coupled to said plate such that said rod extends away from said plate in a substantially horizontal orientation and generally toward said second end of said base;

a face holding assembly being pivotally coupled to and extending away from said second end of said rod, said face holding assembly including a U-shaped member having a central portion and a pair of arms being attached to and extending away from said central portion, wherein said central portion is attached to said rod and is horizontally orientated, a flexible material being removably coupled to and extending along a length of said U-shaped member, wherein the head may be positioned between the arms on said flexible material; and a platform being attached to said upper surface of said base such that said platform is spaced from said upper surface, said platform extending from said second end of said base toward said support frame, said platform being substantially horizontally orientated.

8. A head and neck immobilization device for preventing the movement of a cranial spinal column during radiation applications to the cranial spinal column, said device comprising:

a base having a first end, a second end, an upper surface and a lower surface;

a support frame being attached to and extending upwardly from said upper surface, said support frame being positioned generally adjacent to said first end of said base;

a mounting being positioned on said support frame and being selectively positioned between an upper portion of said support frame and a lower portion of said support frame;

a securing member being adapted for releasably securing said mounting to said frame in a fixed position; and a head support being mounted to and extending outwardly away from said mounting, said head support including a face receiving member for receiving a head in a downward facing position, said head support including an elongated rod having a first end and a second end, said first end being extended into said plate such that said rod extends away from said plate in a substantially horizontal orientation and generally toward said second end of said base, a face holding assembly being pivotally coupled to and extending away from said second end of said rod.

9. The device of claim 8, wherein said support frame includes a plurality of vertically orientated columns.

10. The device of claim 9, wherein each of said columns has a plurality of apertures extending therethrough, each of said apertures being horizontally aligned with one of said apertures in each of said columns, each of said columns having at least three apertures extending therethrough, said securing member comprising a plurality of pins being removably extendable into through said mounting and into one of said apertures.

11. The device of claim 9, wherein each of said columns has a plurality of apertures extending therethrough, each of said apertures being horizontally aligned with one of said apertures in each of said columns, each of said columns having at least three apertures extending therethrough, said mounting comprising a plate having a plurality openings extending therethrough, each of said columns extending through one of said openings in said plate such that said plate is moveably mounted on said columns in a substantially horizontal orientation, said plate having a peripheral edge, each of a plurality of bores extending into said peripheral edge and into one of said openings, wherein each of said bores may be selectively aligned with one of said apertures, said securing member including a plurality of pins, each of said pins being removably extendable into one of said bores and a correspondingly aligned one of said apertures.

12. The device of claim 11, wherein said plurality of columns includes four columns positioned in a generally rectangular configuration, a panel being attached to an upper end of each of columns.

13. The device of claim 8, wherein said face holding assembly includes a U-shaped member having a central portion and a pair of arms being attached to and extending away from said central portion, wherein said central portion is attached to said rod and is horizontally orientated, a flexible material being removably coupled to and extends along a length of said U-shaped member, wherein the head may be positioned between the arms and on said flexible material.

14. The device of claim 10, further including a platform being attached to said upper surface of said base such that said platform is spaced from said upper surface, said platform extending from said second end of said base toward said support frame, said platform being substantially horizontally orientated.

15. The device of claim 8, further including a platform being attached to said upper surface of said base such that said platform is spaced from said upper surface, said platform extending from said second end of said base toward said support frame, said platform being substantially horizontally orientated.

* * * * *